United States Patent
Lee et al.

(10) Patent No.: US 8,030,479 B2
(45) Date of Patent: *Oct. 4, 2011

(54) METHOD OF SEPARATING SMALL RNA MOLECULES USING KOSMOTROPIC SALT

(75) Inventors: Myo-yong Lee, Suwon-si (KR); Nam Huh, Seoul (KR); Joon-ho Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 442 days.
This patent is subject to a terminal disclaimer.

(21) Appl. No.: 12/110,373

(22) Filed: Apr. 28, 2008

(65) Prior Publication Data
US 2009/0131649 A1 May 21, 2009

(30) Foreign Application Priority Data
Nov. 16, 2007 (KR) .................. 10-2007-0117358

(51) Int. Cl.
*C07H 21/00* (2006.01)
(52) U.S. Cl. .................. 536/25.41; 536/25.4
(58) Field of Classification Search .................. None
See application file for complete search history.

(56) References Cited

U.S. PATENT DOCUMENTS

| 5,234,809 A | 8/1993 | Boom et al. |
| 2005/0059024 A1 | 3/2005 | Conrad |
| 2006/0270031 A1 | 11/2006 | Hwang et al. |
| 2007/0043216 A1 | 2/2007 | Bair et al. |
| 2007/0092403 A1* | 4/2007 | Wirbisky et al. ............... 422/65 |
| 2007/0238109 A1 | 10/2007 | Min et al. |
| 2007/0269819 A1 | 11/2007 | Kim et al. |

FOREIGN PATENT DOCUMENTS
DE  10 2005 059 315 A1  6/2007

OTHER PUBLICATIONS

Drager R.R. et al., "High Performance Anion-Exchange Chromatography of Oligonucleotides", Analytical Biochemistry, 1985, pp. 47-56, vol. 145, No. 1, Academic Press, Inc., New York, NY.
Stellrecht, C. et al., "Concurrent Isolation of Ribosomal, Messenger, and Low Molecular Weight RNA", BioTechniques, Nov. 2002, pp. 1122-1124, vol. 33, No. 5, Informa Life Sciences Publishing, Westborough, MA.
Lee M. et al., "Isolation of total RNA from *Escherichia coli* using kosmotropic Hofmeister salts", Analytical Biochemistry, Oct. 2008, pp. 160-162, vol. 381, No. 1.

* cited by examiner

*Primary Examiner* — Patrick Lewis
(74) *Attorney, Agent, or Firm* — Sughrue Mion, PLLC

(57) ABSTRACT

Disclosed is a method of separating small RNAs of 200 nucleotides or less from larger RNAs on a solid support, using a kosmotropic salt of different concentrations.

18 Claims, 4 Drawing Sheets

METHOD OF SEPARATING SMALL RNA MOLECULES USING KOSMOTROPIC SALT

CROSS-REFERENCE TO RELATED PATENT APPLICATION

This application claims the benefit of Korean Patent Application No. 10-2007-0117358, filed on Nov. 16, 2007, in the Korean Intellectual Property Office, the disclosure of which is incorporated herein in its entirety by reference.

BACKGROUND OF THE INVENTION

1. Field of the Invention

The present invention relates to a method of isolating small RNA molecules using a kosmotropic salt, and more particularly, to a method of purifying smaller RNA molecules of 200 nucleotide ("nt") or less from larger RNA molecules on a solid support using a kosmotropic salt.

2. Description of the Related Art

As a method for isolating an RNA, U.S. Patent Application Publication No. 20050059024 A1 discloses a method, wherein nucleic acids are extracted from a cell lysate using phenol and chloroform, and guanidine isothiocyanate and ethanol are added, and is then added to a silica spin column to bind a RNA to the column. Here, small RNA molecules are isolated based on different binding rates between large RNA molecules and small RNA molecules depending on the ethanol content.

The method uses hazardous materials such as phenol, chloroform, and guanidine isothiocyanate, which are chaotropic material, and the procedure to obtain small RNA molecules is very complex.

SUMMARY OF THE INVENTION

The present invention provides a method of isolating small RNA molecules on a solid support using a kosmotropic salt.

According to an embodiment of the present invention, there is provided a method for separating a small RNA molecule from a substance containing the small RNA molecule and a large RNA molecule.

According to an embodiment of the present invention, there is provided a method of isolating a RNA molecule, including (a) contacting a sample containing the RNA molecule with a first solid support in the presence of a kosmotropic salt of a first concentration, the first concentration of the kosmotropic salt being greater than 0.4M; (b) removing the first solid support from the reaction system to give a pre-treated sample containing the RNA molecule; and (c) contacting the pre-treated sample containing the RNA molecule with a second solid support in the presence of a kosmotropic salt of a second concentration to allow the RNA molecule in the pre-treated sample to bind the second solid support, wherein the second concentration of the kosmotropic salt is 0.4M or less.

According to another embodiment of the present invention, there is provided a method of isolating a small RNA molecule including: (a) contacting a sample containing the small RNA molecule with a first solid support in the presence of a kosmotropic salt of a first concentration, the first concentration of the kosmotropic salt being greater than 0.4M; (b) removing the first solid support from the reaction system to give a pre-treated sample containing the small RNA molecule; and (c) contacting the pre-treated sample containing the small RNA molecule with a second solid support in the presence of a kosmotropic salt of a second concentration to allow the small RNA molecule in the pre-treated sample to bind the second solid support, wherein the second concentration of the kosmotropic salt is 0.4M or less.

According to the present invention, the small RNA molecule has about 200 nucleotide residues or less, and the large RNA molecule indicates a RNA molecule having more than about 200 nucleotide residues. The RNA molecules may be single stranded or double stranded.

According to an embodiment of the present invention, the second concentration of the kosmotropic salt may be attained by diluting pre-treated sample obtained in step (b) with an acidic (pH 3-6) diluent containing a kosmotropic salt.

The method may further include eluting the small RNA molecule from the second solid support. A known eluent may be used to elute the small RNA molecule.

In the step (a), the pH may be in the range of from 6 to 9.

In the step (a), a surfactant, such as polysorbate 20 (e.g., TWEEN™ 20) in the concentration of 0.001%-0.05% may be added to the reaction system.

According to an embodiment of the invention, the kosmotropic salt is composed of an anion selected from the group consisting of sulfate ($SO_4^{2-}$), phosphate ($HPO_4^{2-}$), acetate ($CH_3COO^-$), hydroxide ($OH^-$), chloride ($Cl^-$), and formate ($HCOO^-$), and its counter ion.

The present invention also provides a kit for separating a small RNA molecule, which includes a kosmotropic salt and a solid support.

According to another embodiment, there is provided a method of separating a first RNA molecule from a sample containing the first RNA molecule and a second RNA molecule, including (a) contacting the sample with a first solid support in the presence of a kosmotropic salt of a first concentration, the first concentration of the kosmotropic salt being greater than 0.4M to allow the second RNA molecule to bind to the first solid support; (b) removing the first solid support to which the second RNA molecule is bound; and (c) contacting the resultant a pre-treated sample which contains the first RNA molecule, but a substantial amount of the second RNA molecule is removed therefrom, with a second solid support in the presence of a kosmotropic salt of a second concentration to allow the first RNA molecule to bind the second solid support, wherein the second concentration of the kosmotropic salt is 0.4M or less; wherein the first RNA molecule has 200 nucleotide residues or less and the second RNA molecule has more than 200 nucleotide residues; and wherein the kosmotropic salt is a salt of an anion selected from the group consisting of sulfate ($SO_4^{2-}$), phosphate ($HPO_4^{2-}$), acetate ($CH_3COO^-$), hydroxide ($OH^-$), chloride ($Cl^-$), and formate ($HCOO^-$).

According to still another embodiment, there is provided a method of separating a first RNA molecule from a sample containing the first RNA molecule and a second RNA molecule, including (a) contacting a solution containing the sample and a kosmotropic salt of the concentration of greater than 0.4M with a first solid support to allow the second RNA molecule to bind to the first solid support; (b) removing the first solid support to which the second RNA molecule is bound to give a pre-treated solution containing the sample, from which a substantial amount of the second RNA molecule is removed, and the kosmotropic salt; (c) adjusting the concentration kosmotropic salt in the pre-treated solution to reach the range of 0.4M or less; (d) contacting the pre-treated solution of step (c) with a second solid support to allow the first RNA molecule to bind to the second solid support; and (e) removing the second solid support to which the first RNA molecule is bound, wherein the first RNA molecule has 200 nucleotide residues or less and the second RNA molecule has more than 200 nucleotide residues.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
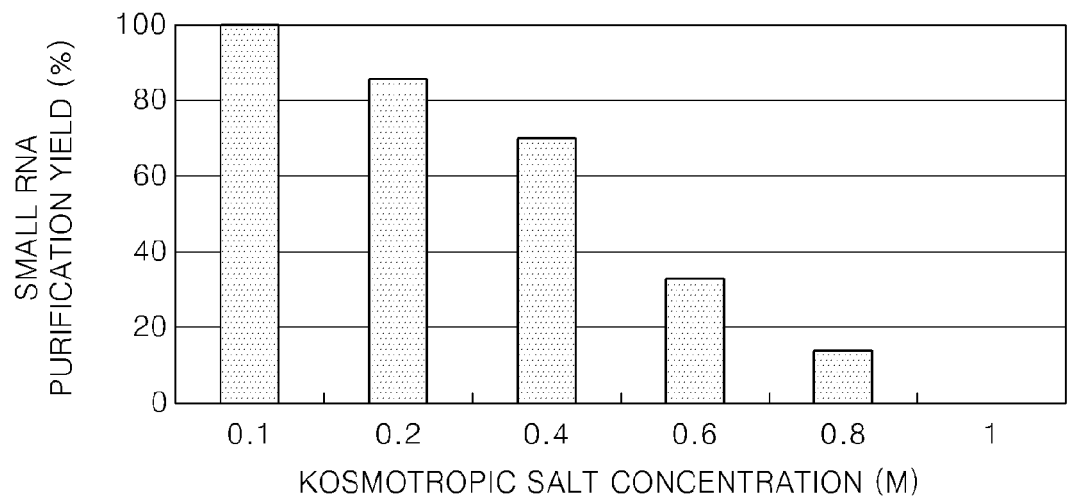
FIG. 1 is a graph illustrating small RNA purification yields with respect to the concentration of a kosmotropic salt.

Hereinafter, the present invention will be described more fully, including with reference to the accompanying Examples, in which preferred embodiments of the invention are shown.

The terms "kosmotrope" or "kosmotropic" (order-maker) and "chaotrope" or "chaotropic" (disorder-maker) are generally used to denote solutes that stabilize or destabilize, respectively, proteins and membranes. Later they referred to the apparently correlating property of increasing, or decreasing respectively, the structuring of water. The term "kosmotropic salt" as employed herein indicates a salt, which has ability to increase water structure. In particular, the salt is formed of an ion which has the same degree of effects on the solubility of a protein in a given solution as kosmotropic ions of Hofmeister series do, and its counterion.

Kosmotropic salts, according to the Hofmeister series, induce protein crystallization, and act as ions for salting-out hydrophobic particles, and form water structures. See, Cacace, M. G. et al., The Hofmeister series: salt and solvent effects on interfacial phenomena, Quart. Rev. Biophys, 30(3), pp. 241-77, (August 1997); Leontidis, E., Hofmeister anion effects on surfactant self-assembly and the formation of mesoporous solids, Curr. Opin. Colloid Interface Sci. 7: 81-91 (2002); Thomas, A. S. & Elcock, A. H., Molecular dynamics simulations of hydrophobic associations in aqueous salt solutions indicate a connection between water hydrogen bonding and the Hofmeister effect. J. Am. Chem. Soc. 129, pp. 14887-98 (2007).

The Hofmeister series is a classification of ions in order of their ability to change water structure. Anions series is as follows: $SO_4^{2-} < HPO_4^{2-} < OH^- < F^- < HCOO^- < CH_3COO^- < Cl^- < Br^- < NO_3^- < I^- < SCN^- < ClO_4^-$. Cations series is: $NH_4^+$, $Rb^+$, $K^+$, $Na^+$, $Cs^+$, $Li^+$, $Ca^{2+}$, $Mg^{2+}$, and $Ba^2$. However, magnesium sulfate and magnesium chloride are excluded from the present invention. The magnesium sulfate and magnesium chloride unexpectedly do not retain the kosmotropic characteristics. The inventors found that magnesium sulfate and magnesium chloride unexpectedly show chaotropic properties. Examples of kosmotropic ions are not limited to those listed in Hofmeister series. Anions or cations having the same degree of effects on secondary and/or tertiary structures of a protein under the same condition to a sulfate ($SO_4^{2-}$), phosphate ($HPO_4^{2-}$), acetate ($CH_3COO^-$), hydroxide ($OH^-$), chloride ($Cl^-$), or formate ($HCOO^-$) may be used. In Hofmeister series, the chaotropic salts randomize the structure of the liquid water and thus tend to decrease the strength of hydrophobic interactions. In contrast, the kosmotrophic salts promote hydrophobic interactions and protein precipitation, due to 'salting-out' or molal surface tension increment effects. Quantification of the Hofmeister (solubility) effect of a salt is usually obtained via linear regression of the relative solubility of a chosen solute (e.g., proteins, peptides, or simple organic molecules) versus the salt's concentration. See for example, E. Leontidis, Hofmeister anion effects on surfactant self-assembly and the formation of mesoporous solids, Current Opinion in Colloid & Interfaces Science 7 (2002) 8191; M. G. Cacace et al., The Hofmeister series: salt and solvent effects on interfacial phenomena, Quarterly Reviews of Biophysics 30 (1997) 241-277; A. S. Thomas and A. H. Elcock, Molecular dynamics simulations of hydrophobic associations in aqueous salt solutions indicate a connection between water hydrogen bonding and the Hofmeister effect, JACS 129 (2007) 14887-14898.

In the present invention, small RNA molecules or small RNAs refer to RNA molecules of 200 nucleotide residues or less.

The method of isolating small RNAs according to the current embodiment of the present invention includes contacting a solution including an RNA-containing sample, which contains a large RNA molecule and a small RNA molecule, and a kosmotropic salt having a concentration of greater than 0.4M with a first solid support, to allow the large RNA to bind to the first solid support. Here, the kosmotropic salt concentration in the solution may be greater than 0.4M. In one embodiment, the concentration may be 0.4M to 2M. The step may be carried out at a pH of 6 to 9. For this purpose, the solution may have a pH 6 to 9, but is not limited thereto. In addition, the step may be carried out in the presence of a surfactant. For example, the solution may include 0.001% to 0.05% of Tween™ 20.

The step of binding the large RNA molecule to the solid support can remove substantial amount of the large RNA molecules from the sample. Here the term "removal of substantial amount of the large RNA molecule" is used to indicate that the resulting RNA-containing sample contains undetectable level, for example, by the detection of Labchip® RNA 6000 Nanokit, of the large RNA molecules/ml of the sample.

The "contact(ing)" refers to not only placing the solution in contact with the surface of the solid support, but also placing the solution through pores of a porous solid support or a solid support in the shape of membrane having pores. In the case of using a porous solid support or a solid support in the shape of membrane having pores, the solution including small RNAs not bound to the solid support is obtained in a form of a filtrate. The RNA-containing sample may be a cell lysate, but is not limited thereto, as long as the sample includes RNA.

The method of isolating small RNAs according to the current embodiment of the present invention further includes separating from the first solid support, the solution including small RNAs not bound to the first solid support. The separation may be performed by a known solid-liquid separation methods such as filtration or centrifugation. For example, the first solid support may be manually removed from the solution, or by centrifuging the solution including the first solid support, thereby removing the first solid support from the solution.

The method of isolating small RNAs according to the current embodiment of the present invention further includes diluting the resulting sample from which the substantial amount of the large RNAs are removed, with a diluent to obtain a diluted kosmotropic salt solution having a concentration of 0.4M or less, and contacting the diluted kosmotropic salt solution with the second solid support to bind small RNAs to the second solid support. The kosmotropic salt concentration of the diluted kosmotropic salt solution may be 0.4M or less. In an embodiment, the concentration may be 0.2M or less. In another embodiment, the concentration may be 10 mM to 0.2M. The diluted kosmotropic salt solution may have an acidic pH, preferably pH 3 to 6. The diluted kosmotropic salt solution may include sodium acetate, but is not limited thereto. The diluent may be acidic, having pH 3 to 6, for example.

The method of isolating small RNAs according to the current embodiment of the present invention further includes applying an elution buffer to the second solid support to which small RNAs are bound, to elute the small RNAs from the second solid support. The elution buffer may be any solution known to those skilled in the art for eluting RNA from a solid support. For example, water, Tris-HCl buffer, phosphate buffered saline (PBS), TE buffer (Tris EDTA buffer) or the like may be used.

The method of isolating small RNAs according to the current embodiment of the present invention may further include first washing with a first wash solution of pH 3 to 6 including a kosmotropic salt having a concentration of 0.4M or less, and then second washing with a second wash solution of pH 6 to 9. The washing steps may be done to the second solid support to which small RNAs are bound, prior to eluting the small RNA from the second solid support. The kosmotropic salt used may be either the same as or different from the kosmotropic salt used in binding large RNAs or binding small RNAs to the first or second solid support, respectively. The kosmotropic salt concentration may be 0.4M or less. In an embodiment, the concentration may be 0.2M or less. In another embodiment, the concentration may be 10 mM to 0.2M, and in particular 10 mM to 0.1M.

The first wash solution may have an acidic pH, for example a pH of 3 to 6. An example of the wash solution may include sodium acetate having a concentration of 10 mM or less. Moreover, the second wash solution used in the second washing may include a buffer of pH 6 to 9, for example, 25 mM Tris buffer (pH 7.4) or 25 mM Tris buffer including ethanol, but is not limited thereto.

The kosmotropic salt used in the method of isolating small RNAs according to the current embodiment of the present invention may be a salt of an anion such as sulfate ($SO_4^{2-}$), phosphate ($HPO_4^{2-}$), acetate ($CH_3COO^-$), hydroxide ($OH^-$), chloride ($Cl^-$), or formate ($HCOO^-$), but is not limited thereto. The same or different kosmotropes may be used when binding large RNAs and when binding small RNAs to the first and second solid support, respectively.

At least a part of the method of isolating small RNAs according to the current embodiment of the present invention may be performed under static or fluidic conditions. Contacting the RNAs with solid supports under static conditions is possible, but contacting the RNAs with solid supports under fluidic conditions is also possible. Fluidic conditions refer to allowing the RNA-containing solution flow within a fluid control system to contact the RNA with the solid supports.

Each of the first and second solid supports to which large RNAs and small RNAs are respectively bound in the present invention may be independently formed of silica, slide glass, silicon wafer, magnetic material, polystyrene, or metal plate, but is not limited thereto. Moreover, each of the first and second solid supports may be flat, but in order to increase the surface contact area between the RNAs and the first and second solid supports to bind more RNAs, the surfaces of the first and second solid supports may be in the form of a multi-pillar structure, bead, or sieve. The first and second solid supports to which large RNAs and small RNAs respectively bind may be the same or different.

According to another embodiment of the present invention, there is provided a small RNA isolation kit including a kosmotropic salt, an acidic diluent, a wash solution, an elution buffer, and a solid support. The diluent may have a pH of 3 to 6, and the wash buffer may include a kosmotropic salt having a concentration of 0.4M or less. The RNA to be isolated may be RNA of 200 nucleotides or less, and the kosmotropic salt may be a salt of an anion selected from the group consisting of sulfate ($SO_4^{2-}$), phosphate ($HPO_4^{2-}$), acetate ($CH_3COO^-$), hydroxide ($OH^-$), chloride ($Cl^-$), or formate ($HCOO^-$), but is not limited thereto. Moreover, the elution buffer may be water or 10 mM Tris buffer.

The present invention will not be described in more detail with reference to the following examples. However, these examples are for illustrative purposes only and are not intended to limit the scope of the invention.

EXAMPLE 1

Effect of Kosmotropic Salt Concentration on Small RNA Purification

According to the protocol provided by a Qiagen™ kit (RNeasy™ Protect Bacteria Mini Kit), lysozymes and proteinase K were treated with *E. coli* to prepare an *E. coli* lysate.

200 μl of the *E. coli* lysate ($1 \times 10^8 \sim 7.5 \times 10^8$ *E. coli* cells) was added to 1 ml of sodium sulfate ($Na_2SO_4$) solution (pH 7.4) each with different concentrations to obtain a mixture solution, and 650 μl of the mixture solution was added to a Qiagen QIAamp™ Mini spin column (silica-gel membrane column), and centrifuged at 8,000 g for 15 seconds. The column was washed with 700 μl of 10 mM $Na_2SO_4$, and washed twice with 25 mM Tris buffer including 80% ethanol (pH 7.4). The column was transferred to a new 1.5 mL Eppendorf tube, and 50 μl of DEPC (diethylpyrocarbonate)-treated water, which inactivates RNase, was added and centrifuged at 8,000 g for 1 minute to elute the total RNA. The amount of small RNAs existing within the total RNA eluate was determined using a small RNA kit Lab chip™ (Agilent Co., USA). The concentrations of the kosmotropic salt, that is, sodium sulfate ($Na_2SO_4$) used in the experiment were 0.1M, 0.2M, 0.4M, 0.6M, 0.8M, and 1M. FIG. 1 is a graph illustrating small RNA purification yields with respect to the concentration of a kosmotropic salt solution used according to Example 1. As shown in FIG. 1, the amount of small RNAs binding to a solid support formed of silica-gel decreases as the kosmotropic salt concentration increases.

EXAMPLE 2

Effect of pH on Small RNA Purification 0.6M $Na_2SO_4$ was dissolved in each of 0.1M NaOAc (pH 3), 0.1M NaOAc (pH 4), 0.1M NaOAc (pH 5.2), 0.1M Tris-HCl (pH 7.4), and 0.1M Tris-HCl (pH 8.8) and the isolation process was performed as in Example 1.

Figure 2:
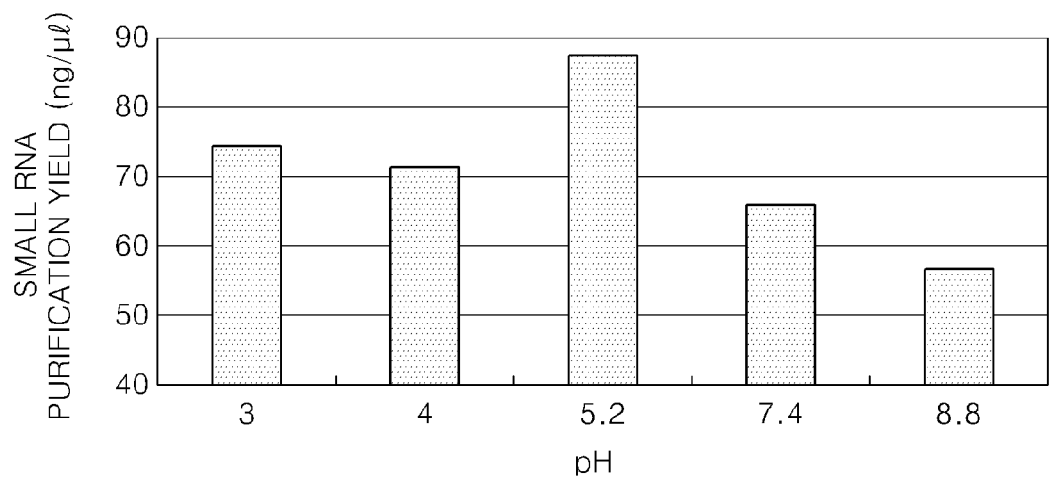
FIG. 2 is a graph illustrating small RNA purification yields with respect to pH of the kosmotropic salt solution.

FIG. 2 is a graph illustrating small RNA purification yields with respect to pH of the kosmotropic salt solution used according to Example 2. As shown in FIG. 2, the amount of small RNAs bound to a solid support formed of silica-gel is larger in acidic binding buffers with pH 7 or less.

EXAMPLE 3

Effect of Surfactants on Small RNA Purification

Polysorbate 20 (Tween™ 20), known to enhance the DNA binding capacity to solid supports, was treated according to different concentrations. A 0.6M $Na_2SO_4$/0.1M Tris-HCl (pH7.4) buffer with 0% to 0.1% of Tween™ 20 was prepared and the isolation process was performed as in Example 1.

Figure 3:
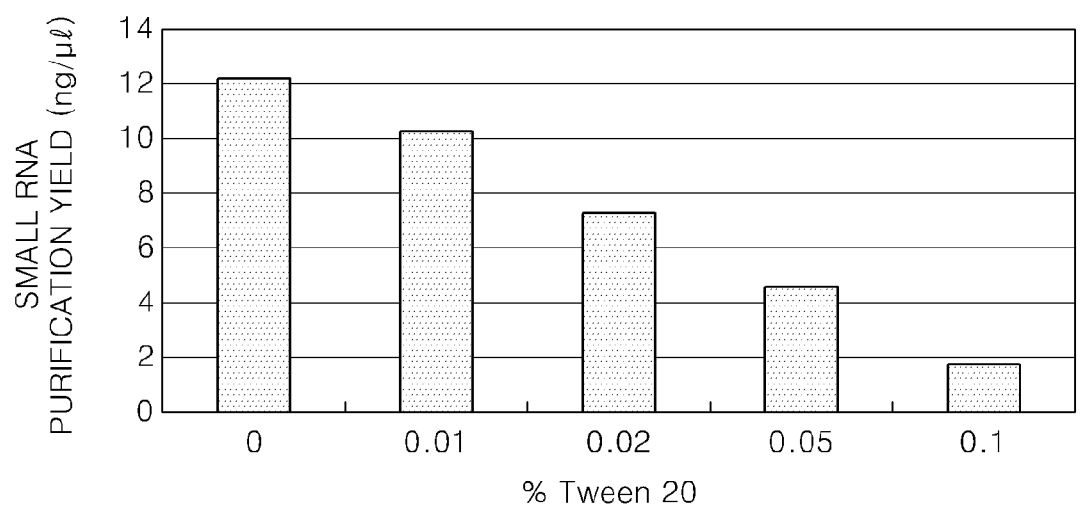
FIG. 3 is a graph illustrating small RNA purification yields with respect to the levels of a surfactant in the kosmotrope solution.

FIG. 3 is a graph illustrating small RNA purification yields with respect to concentration of a surfactant in the kosmotropic salt solution used according to Example 3. As shown in FIG. 3, the amount of small RNA bound to a solid support formed of silica-gel was the largest in the absence of Tween™ 20.

EXAMPLE 4

Small RNA Purification Yield According to the Present Invention

First, the conditions under which small RNAs cannot be bound were selected from Examples 1 through 3 (0.8M $Na_2SO_4$, pH 7.4, then 0.01% Tween™ 20 was selected considering the following small RNA binding). As described in Example 1, 200 μl of the *E. coli* lysate ($1 \times 10^8$–$7.5 \times 10^8$ *E. coli* cells) was mixed with 1 ml of 0.8M $Na_2SO_4$ (pH 7.4), and 650 μl of the mixture solution was added to a Qiagen QIAamp™ Mini spin column (silica-gel membrane column), and centrifuged at 8,000 g for 15 seconds, separating the filtrate from the column.

In order to analyze the material bound to the column, the column obtained by centrifugation above was washed with 700 μl of 10 mM $Na_2SO_4$, and was further washed twice with 25 mM Tris buffer with 80% ethanol (pH 7.4). The column was transferred to a new 1.5 mL Eppendorf tube, and 50 μl of DEPC-treated water inactivating RNase was added and centrifuged at 8,000 g for 1 minute. The RNAs eluted from the column were identified to be large RNAs using an Agilent™ RNA 6000 Nano Kit™. (Lane 2 through 5 of FIG. 4A)

Meanwhile, in order to analyze the material not bound to the column, about 650 μl of the filtrate was diluted by mixing with 5 mL of $H_2O$ and 20 μl of 3M NaOAc (pH 5.2), and 5670 μl of the diluted filtrate was added to the solid support, that is, Qiagen QIAamp™ Mini spin column (silica-gel membrane column). The $Na_2SO_4$ concentration after dilution was 0.08M. After the column was washed with 700 μl of 1 mM NaOAc (pH 4) buffer including 3 mM NaCl, the column was then washed twice with 25 mM Tris buffer (pH 7.4) with 80% ethanol. The column was then transferred to a new 1.5 mL Eppendorf tube, and 50 μl of DEPC-treated water which inactivates RNase was added and centrifuged at 8,000 g for 1 minute. The RNAs eluted from the column were identified to be small RNAs by using an Agilent™ RNA 6000 Nano Kit™ (FIG. 4A Lane 6 through 9).

Figure 4A:
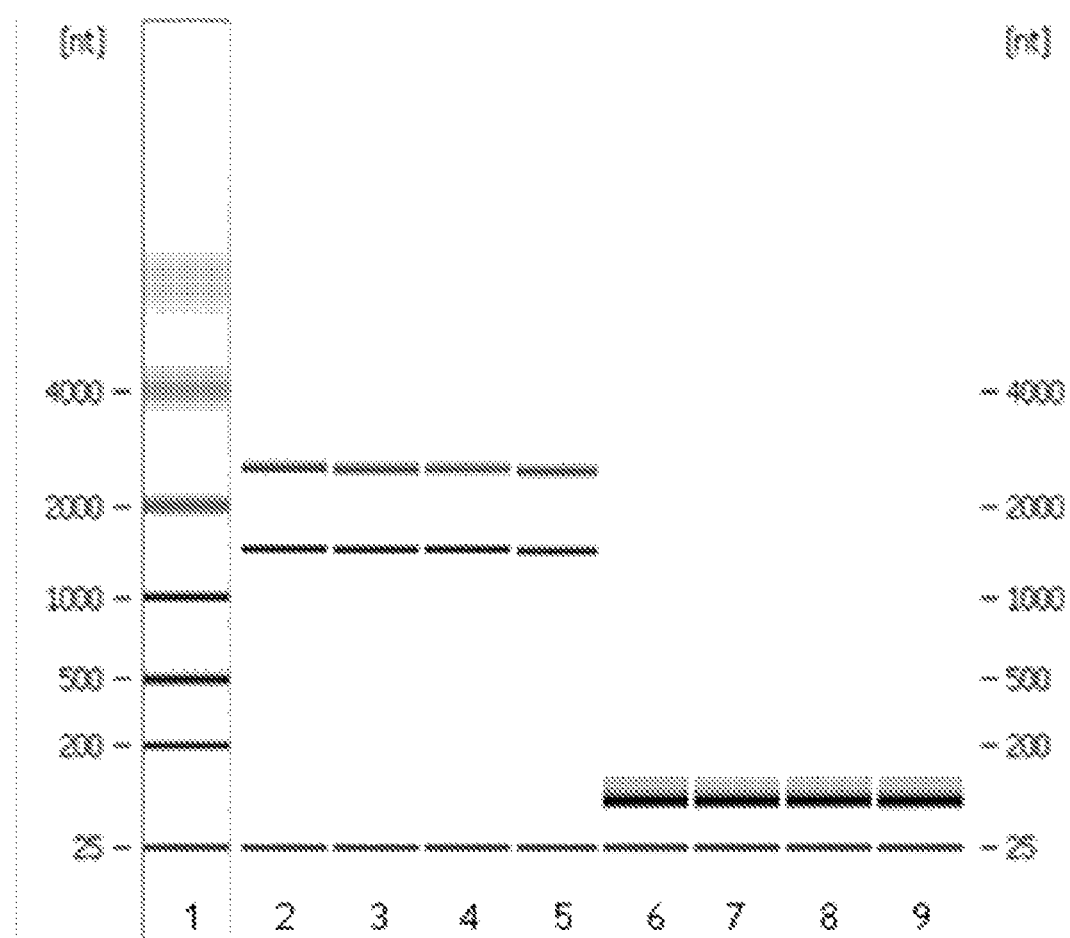
FIG. 4A is an electrophoretogram illustrating the separation of large RNA molecules and small RNA molecules according to the method of the present invention.

FIG. 4A shows that large RNAs and small RNAs are separated without contamination using the Agilent™ RNA 6000 Nano Kit™. In FIG. 4A, lane 1 represents a molecular weight marker, lanes 2 through 5 represent large RNAs, and lanes 6 through 9 represent small RNAs.

Figure 4B:
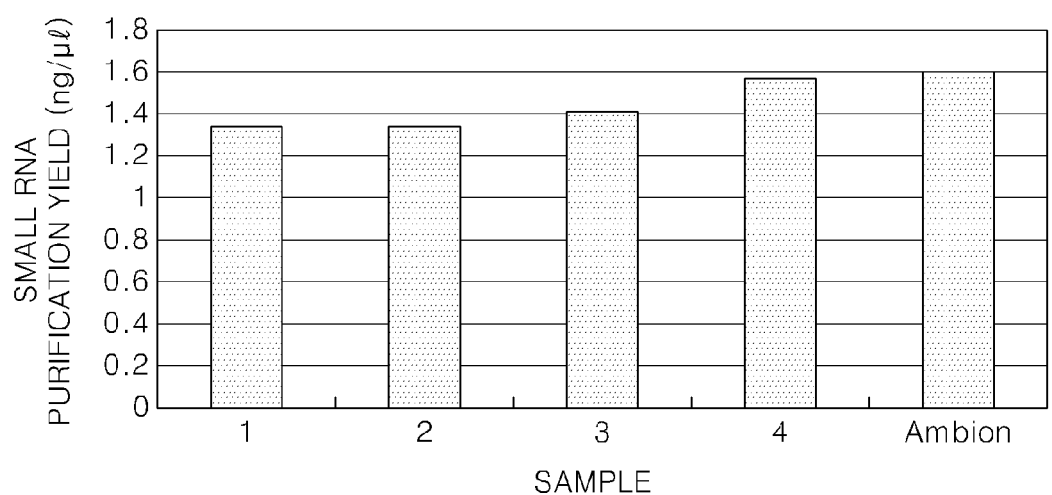
FIG. 4B is a graph comparing the purification yield of small RNA molecules isolated according to the method of the present invention with a conventional method.

FIG. 4B shows that, through the example of the present invention and a comparative example employing commercially available kit (Ambion Co, mirVana™ miRNA Isolation Kit), which is described in US Patent Application Publication No. 20050059024. In FIG. 4B, samples 1 through 4 represent purified RNAs according to Example 4, and the amount of small RNAs is determined using the Agilent™ small RNA kit.

The experiment with a comparative example using the mirVana™ miRNA Isolation Kit by Ambion Co. was performed as follows. Acid-phenol:chloroform was added to 200 μl of *E. coli* lysate, the nucleic acids were extracted, and then only an aqueous solution layer was taken. 100% ethanol was added to the aqueous solution at a content of ⅓ the volume of the aqueous solution and reacted with the solid support to remove large RNAs from the aqueous solution and 100% ethanol was added to the remaining aqueous solution at a content of ⅔ the volume of the remaining solution and reacted with the solid support to bind small RNAs. After the solid support was washed, small RNAs were obtained by eluting small RNAs using 100 μl of the elution buffer included in the kit, at 95° C. Purification yield in FIG. 4B refers to the yield obtained after adjusting the solution volumes to be equal.

According to the present invention, large RNAs and small RNAs may be separated and purified depending on the kosmotropic salt concentration and the pH and nonionic surfactant content of the solid support-binding solution. According to the method of the present invention, small RNAs can be effectively purified while minimizing the contamination of large RNAs.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of isolating small RNAs comprising:
 (a) providing a sample comprising both large and small RNA molecules, wherein the sample is suspended in a buffer comprising a kosmotropic salt at a first concentration, of greater than 0.4M;
 (b) contacting the sample with a first solid support, wherein the large RNA molecules in the sample bind to the first solid support;
 (c) removing the first solid support
 (d) adjusting the kosmotropic salt concentration sample to a second concentration of 0.4M or less;
 (e) contacting the remaining sample with a second solid support, wherein the small RNA molecules in the remaining sample bind to the second solid support, and
 (f) isolating the small RNA molecules bound to the second solid support.

2. The method of claim 1, wherein the isolation of the small RNA molecules bound to the second solid support requires elution of the RNA.

3. The method of claim 1, wherein the first concentration of the kosmotropic salt is 2M or less but greater than 0.4M.

4. The method of claim 1, wherein the sample is a cell lysate.

5. The method of claim 1, wherein the buffer of step (a) has a pH ranging from 6 to 9.

6. The method of claim 1, wherein the buffer of step (a) comprises a surfactant.

7. The method of claim 6, wherein the surfactant is a polysorbate 20 having a concentration of 0.001%-0.05%.

8. The method of claim 1, wherein the kosmotropic salt in steps (a) and (c) is a salt of an anion selected from the group consisting of a sulfate $SO_4^{2-}$, a phosphate $HPO_4^{2-}$, an acetate $CH_3COO^-$, a hydroxide $OH^-$, a chloride $Cl^-$, and a formate $HCOO^-$.

9. The method of claim 1, wherein the second concentration of the kosmotropic salt is 0.2M or less.

10. The method of claim 9, wherein the second concentration of the kosmotropic salt ranges from 10 mM to 0.2M.

11. The method of claim 1, wherein the remaining sample of step (d) is resuspended in a buffer having an acidic pH.

12. The method of claim 11, wherein the pH ranges from 3 to 6.

13. The method of claim 1 further comprising, after step (e), a step of washing the second solid support to which the small RNA molecules are bound with a first wash solution, wherein the first wash solution has a pH ranging from 3 to 6 and comprises a kosmotropic salt at a concentration of 0.4M or less; and then washing the second solid support with a buffer having a pH ranging from 6 to 9.

14. The method of claim 1, wherein the first and second solid supports are each independently formed of a material selected from the group consisting of a silica, slide glass, silicon wafer, magnetic material, polystyrene, and metal plate.

15. The method of claim 1, wherein the first and second solid supports each independently have a shape selected from the group consisting of a flat slide, pillar, bead, and sieve.

16. The method of claim 1, wherein the small RNA molecules are about 200 nucleotides or less in length.

17. The method of claim 1, wherein the sample comprises small RNA molecules of about 200 nucleotide or less in length and large RNA molecules of more than about 200 nucleotides in length.

18. A kit for isolating small RNA molecules comprising a vial comprising a kosmotropic salt; a vial comprising an acidic buffer with a pH of 3 to 6; a vial comprising a wash solution comprising a kosmotropic salt at a concentration of 0.4M or less; a vial comprising an elution buffer; and a solid support, wherein the kosmotropic salt is a salt of an anion selected from the group consisting of a sulfate $SO_4^{2-}$, a phosphate $HPO_4^{2-}$, an acetate $CH_3COO^-$, a hydroxide $OH^-$, a chloride $Cl^-$, and a formate $HCOO^-$.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                                              20
```

-continued

```
<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc rrctgctggc ac                                                    22
```